United States Patent
Møller et al.

(10) Patent No.: US 12,146,194 B2
(45) Date of Patent: Nov. 19, 2024

(54) CIRCULATING SERUM CELL-FREE DNA BIOMARKERS AND METHODS

(71) Applicant: ST. JOHN'S UNIVERSITY, Queens, NY (US)

(72) Inventors: Simon Geir Møller, Queens, NY (US); Ketan Patil, Queens, NY (US)

(73) Assignee: ST. JOHN'S UNIVERSITY, Queens, NY (US)

( * ) Notice: Subject to any disclaimer, the term of this patent is extended or adjusted under 35 U.S.C. 154(b) by 0 days.

(21) Appl. No.: 18/450,103

(22) Filed: Aug. 15, 2023

(65) Prior Publication Data

US 2023/0392208 A1    Dec. 7, 2023

Related U.S. Application Data

(62) Division of application No. 16/977,852, filed as application No. PCT/US2019/021082 on Mar. 7, 2019, now Pat. No. 11,767,562.

(60) Provisional application No. 62/640,205, filed on Mar. 8, 2018.

(51) Int. Cl.
C12Q 1/6883    (2018.01)

(52) U.S. Cl.
CPC ...... *C12Q 1/6883* (2013.01); *C12Q 2600/112* (2013.01); *C12Q 2600/118* (2013.01); *C12Q 2600/158* (2013.01)

(58) Field of Classification Search
None
See application file for complete search history.

(56) References Cited

U.S. PATENT DOCUMENTS

| | | |
|---|---|---|
| 2013/0143214 A1 | 6/2013 | Schuetz |
| 2014/0162933 A1 | 6/2014 | Hatchwell |
| 2014/0274740 A1 | 9/2014 | Srinivasan |
| 2017/0107576 A1 | 4/2017 | Babiarz |

FOREIGN PATENT DOCUMENTS

| | | |
|---|---|---|
| CN | 106434939 A | 2/2017 |
| CN | 107419008 A | 12/2017 |
| JP | 2017-519488 A | 7/2017 |
| JP | 2017-525371 A | 9/2017 |
| WO | 2016/112850 A1 | 7/2016 |
| WO | 2017/083562 A1 | 5/2017 |
| WO | 2017/176630 A1 | 10/2017 |
| WO | 2018/009723 A1 | 1/2018 |
| WO | 2018/039463 A1 | 3/2018 |

OTHER PUBLICATIONS

NCBI Database Accession No. AC096579. National Center for Biotechnology Information, National Library of Medicine, available via URL: < ncbi.nlm.nih.gov/nuccore/AC096579>, 2 pages (Year: 2016).*
NCBI Database Accession No. AC073464. National Center for Biotechnology Information, National Library of Medicine, available via URL: < ncbi.nlm.nih.gov/nuccore/AC073464>, 2 pages (Year: 2005).*
NCBI Database Accession No. AL008628. National Center for Biotechnology Information, National Library of Medicine, available via URL: < ncbi.nlm.nih.gov/nuccore/AL008628>, 1 page (Year: 2013).*
Chen, et al., "Associations among Cognitive Functions, Plasma DNA, and White Matter Integrity in Patients with Early-Onset Parkinson's Disease," Frontiers in Neuroscience, Jan. 2017, 11:9 pp. 1-10.
Klopocki et al., "Copy-Number Variations, Noncoding Sequences, and Human Phenotypes," Annual Reviews Genomics Human Genetics, 2011, 12:53-72.
Lowes et al., "Circulating cell-free mitochondrial DNA levels in Parkinson's disease are influenced by treatment," Molecular Neurodegeneration, 2020, 15:10, pp. 1-8.
Marques, et al., "MicroRNAs in Cerebrospinal Fluid as Potential Biomarkers for Parkinson's Disease and Multiple System Atrophy", Molecular Neurobiology, vol. 54, No. 10 (2016) 7736-45.
Patil, et al., "Combinatory microRNA serum signatures as classifiers of Parkinson's disease", Parkinsonism and Related Disorders, vol. 64 (2019) 202-10.
Pyle, et al., "Reduced Cerebrospinal Fluid Mitochondrial DNA Is a Biomarker for Early-Stage Parkinson's Disease," American Neurological Association, Dec. 2015, 78: 1000-1004.
Wang, et al., "Tiny but Mighty: Promising Roles of MicroRNAs in the Diagnosis and Treatment of Parkinson's Disease", Neuroscience Bulletin, vol. 33, No. 5 (2017) 543-51.

* cited by examiner

*Primary Examiner* — Carla J Myers
(74) *Attorney, Agent, or Firm* — VENABLE LLP

(57) ABSTRACT

Biomarkers and methods for identifying circulating serum-based cfDNA sequences. The cfDNA sequences (PDcRAs) can be used to differentiate patient's suffering from Parkinson's disease (PD) from non-PD patients.

6 Claims, No Drawings

Specification includes a Sequence Listing.

CIRCULATING SERUM CELL-FREE DNA BIOMARKERS AND METHODS

This application is a divisional of U.S. patent application Ser. No. 16/977,852 filed Sep. 3, 2020 which claims benefit of PCT Application No. PCT/US2019/021082 filed Mar. 7, 2019, which in turn claims benefit of U.S. Patent Provisional Application No. 62/640,205 filed Mar. 8, 2018, which are hereby incorporated by reference herein in their entirety.

The instant application contains a Sequence Listing which has been submitted electronically in XML file format and is hereby incorporated by reference in its entirety. Said XML copy, created on Jul. 27, 2023, is named 140415_582842_SL.xml and is 616,366 bytes in size.

BACKGROUND OF THE INVENTION

1. Field of the Invention

The present invention relates to identification and utility of circulating cell-free DNA in serum as diagnostic biomarkers in Parkinson's disease to diagnose the disease and assist the clinicians to determine the treatment options for a subject.

2. Brief Description of the Background Art

Parkinson's disease (PD), the second most common neurodegenerative disease, is a movement disorder characterized by the demise of dopaminergic neurons. Due to unknown etiology and lack of clinical biomarker the current treatment is only for symptomatic relief. L-dopa treatment in addition to other drug combinations alleviates the motor symptoms but cannot reverse or halt the process of neuronal cell death. There are neither any objective tests nor any established biochemical biomarkers for the diagnosis of PD. Further, the heterogeneity, subtypes and the progression of the disease makes it even complex to develop specific therapeutic candidates. Thus it is imperative to diagnose disease at the early stage to increase the efficacy of therapeutic agents as well as to employ new therapies that can be beneficial to patients.

The cell-free DNA (cfDNA) was first detected in blood plasma by Mandel and Metais in 1948 (1). It took many years before the application of cfDNA as a tool for diagnostic purpose. Initial and arguably most successful application of cfDNA was in fetal DNA-based prenatal testing that ranged from sex-determination to detect various genetically linked developmental and other diseases (2). This also points to the fact that the cfDNA found in blood has chimeric origin of diseased as well as healthy cells. cfDNA is highly fragmented, double stranded DNA is mostly 150 bp in length and found freely circulating in the blood. Most fragments of cfDNA correspond to length of nucleosome units, the primary building block of nuclear DNA. This suggests the cell death as major source of cfDNA in blood. This property of cfDNA is key to its application as a diagnostic biomarker especially in diseases associated with cell death or apoptosis. The cfDNA amounts in patient samples could differ and its function remains largely elusive after 70 years since initial discovery. Since there are factors like sample collection, blood cell lysis that can affect the cfDNA yield in plasma samples, serum can be an alternative source for biomarker discovery.

SUMMARY OF THE INVENTION

It is an object of the present invention to identify serum cfDNA sequences relevant to patients suffering from Parkinson's disease.

It is another object of the present invention to provide methods for determining patients suffering from Parkinson's disease.

These objects and others are achieved by the present invention, which provides circulating cfDNA biomarkers that may be used singly, in pairs or in combination to determine patients suffering from Parkinson's disease.

DETAILED DESCRIPTION OF THE INVENTION

Unless defined otherwise, all technical and scientific terms used herein have the meaning commonly understood by a person skilled in the art to which this invention belongs. The following references provide one of skill with a general definition of many of the terms used in this invention: Singleton et al., *Dictionary of Microbiology and Molecular Biology* (2nd ed. 1994); *The Cambridge Dictionary of Science and Technology* (Walker ed., 1988); *The Glossary of Genetics*, 5th Ed., R. Rieger et al. (eds.), Springer Verlag (1991); and Hale & Marham, *The Harper Collins Dictionary of Biology* (1991). As used herein, those following terms have the meanings ascribed to them unless specified otherwise.

Methods

Serum Samples Handling and Classification

All patients and controls participated in the Norwegian ParkWest project, which are ongoing prospective population-based longitudinal cohort studies investigating the incidence, neurobiology and prognosis of PD. The Norwegian ParkWest study is a prospective longitudinal multicenter cohort study of patients with incident Parkinson's disease (PD) from Western and Southern Norway. Between Nov. 1, 2004 and 31 Aug. 2006 it was endeavored to recruit all new cases of Parkinson Disease within the study area. Since the start of the study 212 of 265 (80%) of these patients and their age-/sex-matched control group have been followed. Further information about this project can be found at http://www.parkvest.no.

All possible efforts were undertaken to establish an unselected and population-representative cohort of patients with PD. Patients were included if they had provided serum at study entry and fulfilled diagnostic criteria for PD of the National Institute of Neurological Disorders and Stroke (http://www.ninds.nih.gov/disorders/parkinsons_disease/parkisons_disease.htm) and UK Brain Bank (http://www.ncbi.nlm.nih.gov/projects/gap/cgi-bin/GetPdf.cgi?id=phd000042) at latest follow-up. Patients with secondary parkinsonism at study entry were excluded from this study. Control subjects were recruited from multiple sources, including friends, spouses, and public organizations for elderly and were included in this study if they had provided serum. All patients and controls were Caucasian.

In this study of possible biomarkers for PD we utilized serum from 6 patients and 3 controls which were selected at random.

Serum samples were collected at the same day as the clinical examinations and then stored frozen at −70 degrees Celsius until transported to the facilities in New York on dry ice.

Example 1: Analyses of Differential Levels of Human cfDNA by NGS cfDNA Isolation from Serum Samples and QC After thawing on ice, nine (three control, six PD samples) serum samples were spun down for 5 mins at 3000×g to remove debris. The supernatant was used to perform cfDNA isolation using E-Z Nucleic Acid (E.Z.N.A.®) circulating DNA Isolation Kit (Omega Bio-tek, GA). Before DNA Isolation, the samples were spiked with 0.1 pg/ul of spike-in control DNA (L34, *Zea mays*). The remaining part of the RNA isolation was performed following manufacturer's protocol. The isolated cfDNA was quantified on a Qubit 4 Fluorometer (Thermo Scientific, MA) and quality of the cfDNA was assessed by Alu assay and High sensitivity Bioanalyzer DNA assay (Agilent, CA). The cfDNA was then used for library preparation.

Library Prep, QC and Sequencing

The isolated cfDNA (15 ng) from nine patient serum samples were subjected to sequencing library preparation using Accel-NGS® 2S Plus DNA Library Kit (Swift Biosciences, MI) following manufacturer's protocol. The prepared libraries were quality checked and quantified using Qubit 4 Fluorometer (Thermo Scientific, MA), KAPA Library Quantification Kits (KAPA Biosystems, MA) and Agilent 4200 TapeStation System (Agilent, CA). The spike-in control was recovered at consistent levels for all the samples. The cfDNA libraries were sequenced using HiSeq 4000 Paired-End 100 or PE150 Cycle lanes (Illumina, CA) at NYU School of Medicine's Genome Technology Center (https://med.nyu.edu/research/scientific-cores-shared-resources/genome-technology-center). The fastq.gz files obtained from sequencing runs were imported into Partek Flow (Partek, MO) for analysis.

NGS Data Analysis

Paired end sequencing data was imported into Partek Flow for data analysis. Quality control analysis demonstrated a read depth range of 47,627,391-100,811,153, with a mean depth of 83,311,383. The data was also checked to ensure appropriate sequence quality with regards to average base score quality, the percent of missing bases, and GC content. Alignment of sequencing reads to the hg19 version of the human genome assembly was performed using default parameters of the MEM algorithm in the BWA aligner version 0.7.15 (3, 4). Post alignment quality control demonstrated an average alignment rate of 98.74% (min: 98.36%, max: 99.22%), primarily composed of alignments mapping to a unique location (mean: 94.65%, min: 93.00%, max: 95.94%). The coverage of the genome ranged from 88.02%-92.08% (mean: 91.15%), with an average coverage depth of 8.60 (min: 5.08, max: 10.26). The aligned reads were then filtered to remove duplicate reads in the data set. DNA copy number analysis was performed independently for each sample utilizing Control-FREEC version 11.0, using default parameters and a window of 5 kb (5). The resulting segment ratios of regions of copy number imbalance were imported into Partek Genomics Suite version 6.6, and data was filtered to exclude identified regions of gain and loss found in control sample. Recurrent regions of gain and loss were then identified to determine regions conserved across all cases and those unique to either moderate or severe groups. These regions of copy number imbalance were then annotated with regards to their proximity to gene content utilizing the RefSeq.

Differentially Expressed Human cfDNA Sequences

The differentially expressed human cfDNA sequences in Parkinson's disease patients' serum samples from The Norwegian ParkWest study were determined employing NGS. Table 1 below illustrates the cfDNA sequences with statistically significant differential levels in PD patient serum samples obtained by methods explained in [00010]. The identified chromosomes that were used for data analysis are known to those of ordinary skill herein from the human genome sequence (hg19—Genome Reference Consortium Human Build 37 (GRCh37)) found at https://www.ncbi.nlm.nih.gov/assembly/GCF_000001405.13/

TABLE 1

| Seq. ID. | Chromosome | Seq. Start | Seq. Stop | Average Relative Copy Number | Fold change in levels |
|---|---|---|---|---|---|
| 1 | 2 | 37960000 | 37965000 | 3.658 | 1.829 |
| 2 | 2 | 37965000 | 37970000 | 3.658 | 1.829 |
| 3 | 2 | 37970000 | 37975000 | 3.658 | 1.829 |
| 4 | 2 | 37975000 | 37980000 | 3.658 | 1.829 |
| 5 | 2 | 37980000 | 37985000 | 3.658 | 1.829 |
| 6 | 2 | 37985000 | 37990000 | 3.658 | 1.829 |
| 7 | 2 | 37990000 | 37995000 | 3.658 | 1.829 |
| 8 | 2 | 37995000 | 38000000 | 3.658 | 1.829 |
| 9 | 2 | 38000000 | 38005000 | 3.658 | 1.829 |
| 10 | 2 | 89070000 | 89075000 | 4.132 | 2.066 |
| 11 | 2 | 89075000 | 89080000 | 4.132 | 2.066 |
| 12 | 2 | 89080000 | 89085000 | 4.132 | 2.066 |
| 13 | 2 | 95470000 | 95475000 | 5.136 | 2.568 |
| 14 | 2 | 95475000 | 95480000 | 5.136 | 2.568 |
| 15 | 2 | 98125000 | 98130000 | 4.297 | 2.149 |
| 16 | 2 | 98130000 | 98135000 | 4.297 | 2.149 |
| 17 | 3 | 40245000 | 40250000 | 7.275 | 3.637 |
| 18 | 3 | 46160000 | 46165000 | 7.435 | 3.718 |
| 19 | 4 | 5315000 | 5320000 | 8.866 | 4.433 |
| 20 | 4 | 27695000 | 27700000 | 4.963 | 2.482 |
| 21 | 6 | 29685000 | 29690000 | 4.569 | 2.285 |
| 22 | 6 | 162295000 | 162300000 | 8.784 | 4.392 |
| 23 | 6 | 170705000 | 170710000 | 7.853 | 3.927 |
| 24 | 8 | 144750000 | 144755000 | 4.551 | 2.275 |
| 25 | 8 | 7095000 | 7100000 | 1.282 | 0.641 |
| 26 | 8 | 7100000 | 7105000 | 1.325 | 0.663 |
| 27 | 8 | 7105000 | 7110000 | 1.325 | 0.663 |
| 28 | 8 | 7110000 | 7115000 | 1.325 | 0.663 |
| 29 | 8 | 7115000 | 7120000 | 1.325 | 0.663 |
| 30 | 8 | 7120000 | 7125000 | 1.325 | 0.663 |
| 31 | 8 | 7125000 | 7130000 | 1.325 | 0.663 |
| 32 | 8 | 7130000 | 7135000 | 1.325 | 0.663 |
| 33 | 8 | 7135000 | 7140000 | 1.325 | 0.663 |
| 34 | 8 | 7140000 | 7145000 | 1.325 | 0.663 |
| 35 | 8 | 7145000 | 7150000 | 1.325 | 0.663 |
| 36 | 8 | 7150000 | 7155000 | 1.325 | 0.663 |
| 37 | 8 | 7155000 | 7160000 | 1.325 | 0.663 |
| 38 | 8 | 7160000 | 7165000 | 1.325 | 0.663 |
| 39 | 8 | 7165000 | 7170000 | 1.325 | 0.663 |
| 40 | 8 | 7170000 | 7175000 | 1.325 | 0.663 |
| 41 | 8 | 7175000 | 7180000 | 1.325 | 0.663 |
| 42 | 8 | 7180000 | 7185000 | 1.325 | 0.663 |
| 43 | 8 | 7185000 | 7190000 | 1.325 | 0.663 |
| 44 | 8 | 7190000 | 7195000 | 1.325 | 0.663 |
| 45 | 8 | 7195000 | 7200000 | 1.325 | 0.663 |
| 46 | 9 | 69680000 | 69685000 | 4.481 | 2.240 |
| 47 | 9 | 69685000 | 69690000 | 4.481 | 2.240 |
| 48 | 9 | 40815000 | 40820000 | 1.116 | 0.558 |
| 49 | 9 | 40820000 | 40825000 | 1.116 | 0.558 |
| 50 | 9 | 40825000 | 40830000 | 1.116 | 0.558 |
| 51 | 9 | 40830000 | 40835000 | 1.116 | 0.558 |
| 52 | 10 | 119940000 | 119945000 | 4.837 | 2.419 |
| 53 | 11 | 106580000 | 106585000 | 5.750 | 2.875 |
| 54 | 11 | 119610000 | 119615000 | 4.945 | 2.473 |
| 55 | 12 | 38150000 | 38155000 | 2.653 | 1.327 |
| 56 | 12 | 38155000 | 38160000 | 2.653 | 1.327 |
| 57 | 12 | 38160000 | 38165000 | 2.653 | 1.327 |
| 58 | 12 | 38165000 | 38170000 | 2.653 | 1.327 |
| 59 | 12 | 38170000 | 38175000 | 2.653 | 1.327 |
| 60 | 12 | 38175000 | 38180000 | 2.653 | 1.327 |
| 61 | 12 | 38180000 | 38185000 | 2.653 | 1.327 |
| 62 | 12 | 38185000 | 38190000 | 2.653 | 1.327 |
| 63 | 12 | 38190000 | 38195000 | 2.653 | 1.327 |
| 64 | 12 | 38195000 | 38200000 | 2.653 | 1.327 |
| 65 | 12 | 38200000 | 38205000 | 2.653 | 1.327 |
| 66 | 12 | 38205000 | 38210000 | 2.653 | 1.327 |
| 67 | 12 | 38210000 | 38215000 | 2.653 | 1.327 |
| 68 | 12 | 38215000 | 38220000 | 2.653 | 1.327 |
| 69 | 12 | 38220000 | 38225000 | 2.653 | 1.327 |
| 70 | 12 | 38225000 | 38230000 | 2.653 | 1.327 |

TABLE 1-continued

| Seq. ID. | Chromosome | Seq. Start | Seq. Stop | Average Relative Copy Number | Fold change in levels |
|---|---|---|---|---|---|
| 71 | 12 | 38230000 | 38235000 | 2.653 | 1.327 |
| 72 | 12 | 38235000 | 38240000 | 2.653 | 1.327 |
| 73 | 12 | 38240000 | 38245000 | 2.653 | 1.327 |
| 74 | 13 | 53685000 | 53690000 | 3.635 | 1.817 |
| 75 | 14 | 34815000 | 34820000 | 6.120 | 3.060 |
| 76 | 14 | 106780000 | 106785000 | 3.412 | 1.706 |
| 77 | 14 | 106785000 | 106790000 | 3.412 | 1.706 |
| 78 | 14 | 106790000 | 106795000 | 3.412 | 1.706 |
| 79 | 14 | 106795000 | 106800000 | 3.450 | 1.725 |
| 80 | 14 | 106800000 | 106805000 | 3.450 | 1.725 |
| 81 | 14 | 106805000 | 106810000 | 3.450 | 1.725 |
| 82 | 15 | 84855000 | 84860000 | 3.840 | 1.920 |
| 83 | 15 | 84860000 | 84865000 | 3.840 | 1.920 |
| 84 | 15 | 84865000 | 84870000 | 3.840 | 1.920 |
| 85 | 17 | 41535000 | 41540000 | 5.425 | 2.712 |
| 86 | 17 | 43590000 | 43595000 | 4.612 | 2.306 |
| 87 | 17 | 34670000 | 34675000 | 1.143 | 0.571 |
| 88 | 18 | 19790000 | 19795000 | 4.416 | 2.208 |
| 89 | 19 | 19885000 | 19890000 | 3.685 | 1.842 |
| 90 | 19 | 52135000 | 52140000 | 0.216 | 0.108 |
| 91 | 19 | 52140000 | 52145000 | 0.216 | 0.108 |
| 92 | 19 | 52145000 | 52150000 | 0.216 | 0.108 |
| 93 | 22 | 17235000 | 17240000 | 4.942 | 2.471 |
| 94 | 22 | 24275000 | 24280000 | 0.925 | 0.463 |
| 95 | 22 | 24280000 | 24285000 | 0.925 | 0.463 |
| 96 | 22 | 24285000 | 24290000 | 0.925 | 0.463 |
| 97 | 22 | 24290000 | 24295000 | 1.083 | 0.542 |
| 98 | 22 | 24295000 | 24300000 | 1.083 | 0.542 |
| 99 | 22 | 24300000 | 24305000 | 1.083 | 0.542 |
| 100 | 22 | 24305000 | 24310000 | 1.083 | 0.542 |
| 101 | 22 | 24310000 | 24315000 | 1.083 | 0.542 |
| 102 | 22 | 24315000 | 24320000 | 1.083 | 0.542 |
| 103 | 22 | 24320000 | 24325000 | 1.083 | 0.542 |
| 104 | 22 | 24325000 | 24330000 | 1.083 | 0.542 |
| 105 | 22 | 24330000 | 24335000 | 1.077 | 0.538 |

Note:
Copy number is the average copy number in PD serum samples assuming the copy number for control samples as 2.

Example 2

Measurement of levels of a combination of many cfDNA sequences in serum from patients can assist or improve the accuracy in distinctly differentiating between a potential PD patient and a healthy individual. A serum sample is obtained from blood withdrawn from patients suspected of PD. The serum is used for total cfDNA isolation and enrichment. This RNA would then be tested using NGS or qPCR to measure the levels of any two or more of the 105 cfDNA sequences mentioned in Example 1.

Detectable levels of any two or more of the 105 cfDNA sequences confirms the patient has PD. If desired, other sample fluids may be utilized, including plasma, venous or arterial blood, or CSF samples withdrawn by lumbar puncture. Such plasma, blood or CSF samples are processed as above. It will be understood that measurement of more than two cfDNA sequences in combination or a set of combinations used in a test matrix may desirably increase the accuracy of PD diagnosis. Similarly, practitioners of ordinary skill herein will further appreciate that shorter DNA sequences within any of the identified cfDNA sequences may desirably be utilized instead of the entire cfDNA sequence. These shorter DNA sequences are preferably unique to the SEQ ID NO. in which they are found, and may have lengths on the order of about 1000 bp, 900 bp, 800 bp, 700 bp, 600 bp, 500 bp, 400 bp, 300 bp, 200 bp, 100 bp, 50 bp or 25 bp.

Example 3

A microarray tray is provided containing labeled nucleotide sequences that are antisense to selected cfDNA SEQ ID NOS. among cfDNA SEQ ID NOS. 1-105. The labeled antisense nucleotide sequences may be antisense to shorter DNA sequences found with the selected cfDNA SEQ ID NOS., which shorter DNA sequences are preferably unique to the cfDNA sequences encompassing them. Alternatively, the microarray tray may contain labeled antibodies that specifically bind selected cfDNA SEQ ID NOS. among cfDNA SEQ ID NOS. 1-105. The labeled antibodies may specifically bind shorter DNA sequences found with the selected cfDNA SEQ ID NOS., which shorter DNA sequences are preferably unique to the cfDNA sequences encompassing them. The term "antibody" includes both polyclonal and monoclonal antibodies. The phrase "specifically (or selectively) binds" refers to a binding reaction between two molecules that is at least two times the background and more typically more than 10 to 100 times background molecular associations under physiological conditions. Specific binding is determinative of the presence of the DNA or cfDNA, in a heterogeneous population cfDNAs. Thus, under designated immunoassay conditions, the specified antibodies bind to a particular DNA sequence, thereby identifying its presence as well as the presence of the cfDNA encompassing it. Specific binding antibodies may be characterized by having specific binding activity ($K_a$) of at least about $10^5$ $M^{-1}$, $10^6$ $M^{-1}$ or greater, preferably $10^7$ $M^{-1}$ or greater, more preferably 108 $M^{-1}$ or greater, and most preferably 109 $M^{-1}$ or greater. The binding affinity of an antibody can be readily determined by one of ordinary skill in the art, for example, by Scatchard analysis (Scatchard, Ann. NY Acad. Sci. 51: 660-72, 1949). Methods of making antibodies are well known to those skilled in the art (Winter and Harris, Immunol. Today 14:243-246 (1993); Ward et al., Nature 341:544-546 (1989); Harlow and Lane, supra, 1988; Hilyard et al., Protein Engineering: A practical approach (TRL Press 1992); Borrabeck, Antibody Engineering, 2d ed. (Oxford University Press 1995); each of which is incorporated herein by reference).

Example 4

Many neurodegenerative diseases are closely related to each other when it comes to symptoms as well as pathological markers. The circulating diagnostic markers for one neurodegenerative disease can be useful for diagnosis of other disease. A method to diagnose other neurodegenerative diseases like Dementia with Lewy body (DLB), Amyotrophic lateral sclerosis (ALS), Alzheimer's disease (AD), Multiple system atrophy (MSA), CorticoBasal Degeneration (CBD), Progressive Supranuclear Palsy (PSP) can also be developed using similar cfDNA sequences measurements of candidates mentioned above. Disease specific kits can be developed similar to one mentioned in [0014] with various combinations of DNA or cfDNA sequences listed in [0012] and [0013].

Example 5

The absence or presence of one or more combinations of DNA or cfDNA sequences in PD patient samples as compared to control samples can be used to develop disease specific kit as mentioned in [0014].

Example 6

The function of the cfDNA sequences which may cross blood brain barrier depending on the size of molecule is poorly understood but a disease specific sequence can be targeted for understanding PD etiology and to target them for therapy.

Example 7

Small nucleic acid molecules derived from cfDNA sequences mentioned in [0012] and [0013] will be designed to therapeutically intervene by specifically targeting genes in PD brains to achieve complete or partial remedy.

---

SEQUENCE LISTING

The patent contains a lengthy sequence listing. A copy of the sequence listing is available in electronic form from the USPTO web site (https://seqdata.uspto.gov/?pageRequest=docDetail&DocID=US12146194B2). An electronic copy of the sequence listing will also be available from the USPTO upon request and payment of the fee set forth in 37 CFR 1.19(b)(3).

---

What is claimed is:

1. A method for treating Parkinson's disease in a human patient, comprising the steps of:
    obtaining a sample from said human patient, said sample being serum or plasma; and
    identifying differential levels of at least one of SEQ ID NOS: 12, 13 and 23 within said sample compared to those of a healthy control;
    diagnosing the human patient as having Parkinson's disease based on the detection of differential levels of at least 2.066, 2.568 and 3.927 fold, respectively, in the sample above that of the healthy control for the identified sequence among SEQ ID NOS: 12, 13 and 23; and
    administering L-dopa therapy to the human patient diagnosed as having Parkinson's disease.

2. The method according to claim 1, wherein the differential level of said DNA sequences is determined using direct quantitative real time PCR in said sample.

3. The method according to claim 1, wherein the differential level of said DNA sequences is determined using quantitative real time PCR.

4. The method according to claim 1, wherein the differential level of said DNA sequences is determined using labeled antisense nucleotide sequences.

5. The method according to claim 1, wherein the differential level of said DNA sequences is determined using microarray profiling.

6. The method according to claim 1, wherein the differential level of said DNA sequences is determined using high throughput NGS sequencing.

* * * * *